US00PP26530P3

(12) United States Plant Patent
McLane

(10) Patent No.: US PP26,530 P3
(45) Date of Patent: Mar. 22, 2016

(54) WATER LILY PLANT NAMED 'PURPLE FANTASY'

(50) Latin Name: ***Nymphaea* hybrid**
Varietal Denomination: Purple Fantasy

(71) Applicant: Florida Aquatic Nurseries, Inc., Fort Lauderdale, FL (US)

(72) Inventor: Brandon McLane, Fort Lauderdale, FL (US)

(73) Assignee: Florida Aquatic Nurseries, Inc., Fort Lauderdale, FL (US)

( * ) Notice: Subject to any disclaimer, the term of this patent is extended or adjusted under 35 U.S.C. 154(b) by 79 days.

(21) Appl. No.: 13/999,493

(22) Filed: Mar. 3, 2014

(65) Prior Publication Data

US 2015/0250086 P1 Sep. 3, 2015

(51) Int. Cl.
*A01H 5/02* (2006.01)

(52) U.S. Cl.
USPC ..... Plt./342

(58) Field of Classification Search
USPC ..... Plt./342
See application file for complete search history.

*Primary Examiner* — Susan McCormick Ewoldt
(74) *Attorney, Agent, or Firm* — Yau Law Firm; Jo-Anne Yau

(57) ABSTRACT

A new and distinct cultivar of *Nymphaea* water lily plant characterized by its purple flowers, growth habit, rhizome, and cold hardiness.

6 Drawing Sheets

Genus and species: *Nymphaea* hybrid.

Varietal name: 'Purple Fantasy'.

My new variety resulted from an intentional cross of *Nymphaea* 'Bernice Ikins' (unpatented, seed parent) and *Nymphaea* '109' (an unpatented hybrid variety, pollen parent).

The cross that resulted in the seed for this plant was made in Davie, Broward County, Fla. in 2011. My new plant was first asexually propagated by rhizome division in Davie, Fla. in 2012. Since then, reproduction of this plant by rhizome division in Davie, Fla. has confirmed that the new variety of water lily is a stable hybrid. That is, no evidence of off-types of the new variety has been observed. Thus, the new variety is stable and reproduces true to type in successive generations of asexual reproduction.

My new variety is distinguished by purple flowers in combination with a growth habit, rhizome, and cold hardiness typical of 'Bernice Ikins'.

Comparison to parents: The seed parent 'Bernice Ikins' has a pink to red flower. The new variety differs from the seed parent by having a flower that is purple in color and more stellate in shape. Also, the sinus gap of my new variety is much wider in the leaf than the sinus gap of 'Bernice Ikins'. The new variety differs from the pollen parent *Nymphaea* '109' by having a flower shape that is more stellate with fewer flower petals. The leaves of my new variety are thicker than those of *Nymphaea* '109' and resemble leaves of 'Bernice Ikins' in texture. The pedicel and peduncle of my new variety are pubescent similar to those in subgenus *Nymphaea*. My new plant spreads by a rhizome like the seed plant 'Bernice Ikins'. My new plant is also cold hardy like the seed parent.

Insofar as I am aware, there has been no purple cold hardy *Nymphaea* water lily available for the water garden market. Water lilies of the subgenus brachyceras are known to have purple flowers, but brachyceras lily plants are not cold hardy.

The description herein is of progeny of the original plant that have been observed growing under cultivation in Davie, Fla.

Certain characteristics of this variety, such as growth and color, may change with changing environmental conditions (e.g., light, temperature, moisture, nutrient availability, or other factors). Color descriptions and other terminology are used in accordance with their ordinary dictionary descriptions, unless the context clearly indicates otherwise. Color designations are made with reference to The Royal Horticultural Society (R.H.S.) Colour Chart, copyright 1986.

BOTANICAL DESCRIPTION

Figure 1:
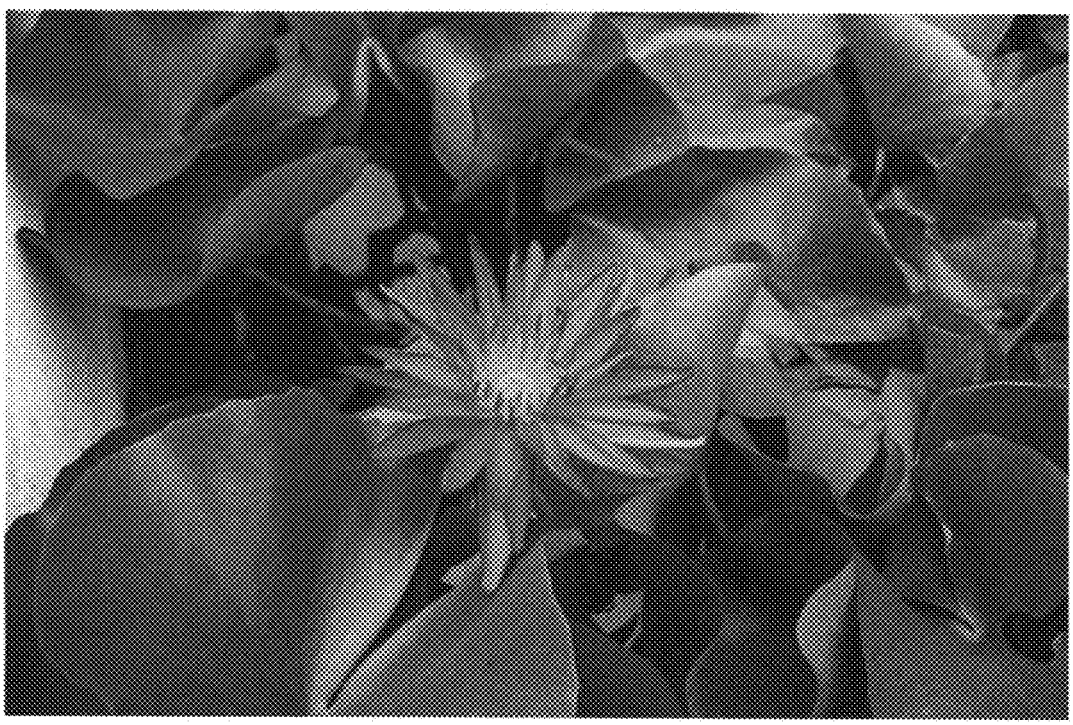
FIG. 1 is a close up view of a flower and number of leaves of a plant of my new variety, at the approximate age of one year.
Figure 2:
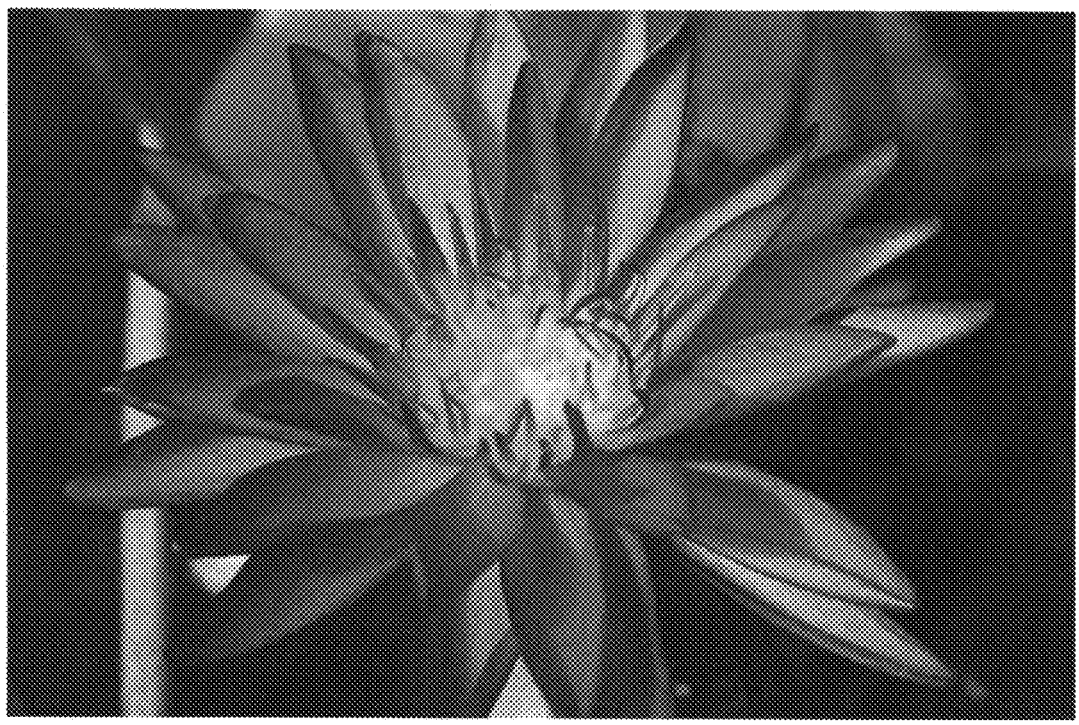
FIG. 2 is an even closer view of one flower of my new variety at the approximate age of one year.
Figure 3:
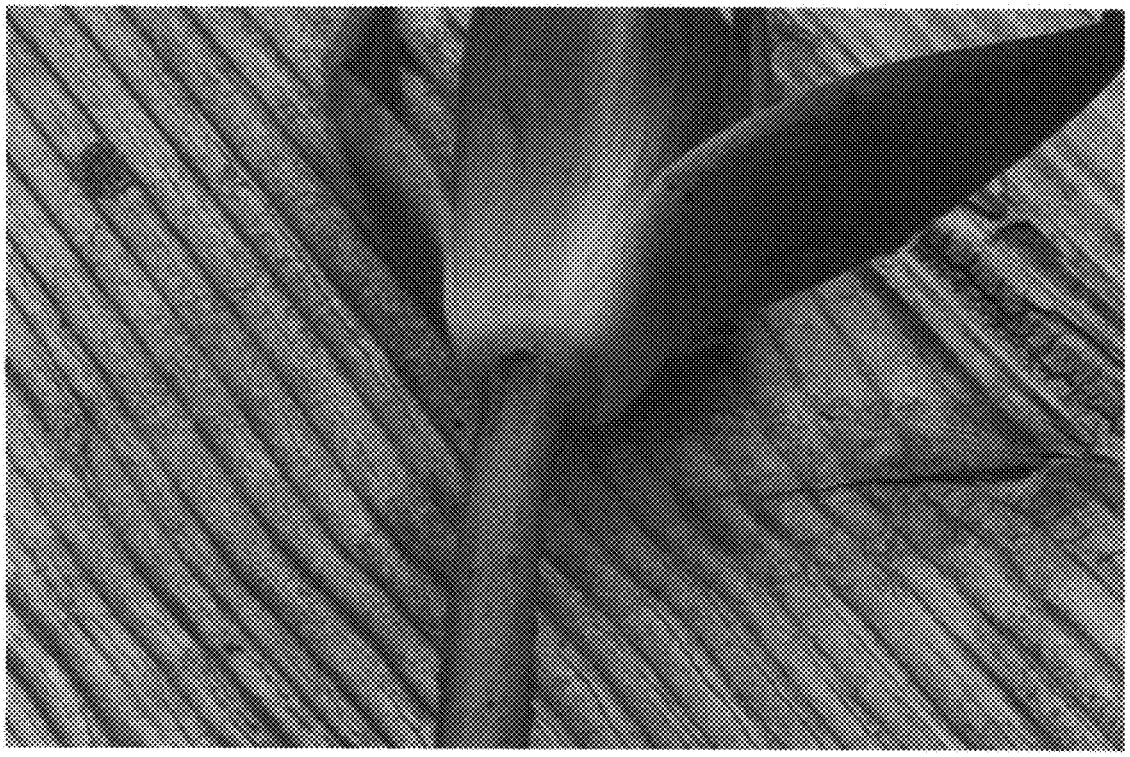
FIG. 3 is a close up view of the top of the peduncle and the underside of the sepals of my new variety at the approximate age of one year.
Figure 4:
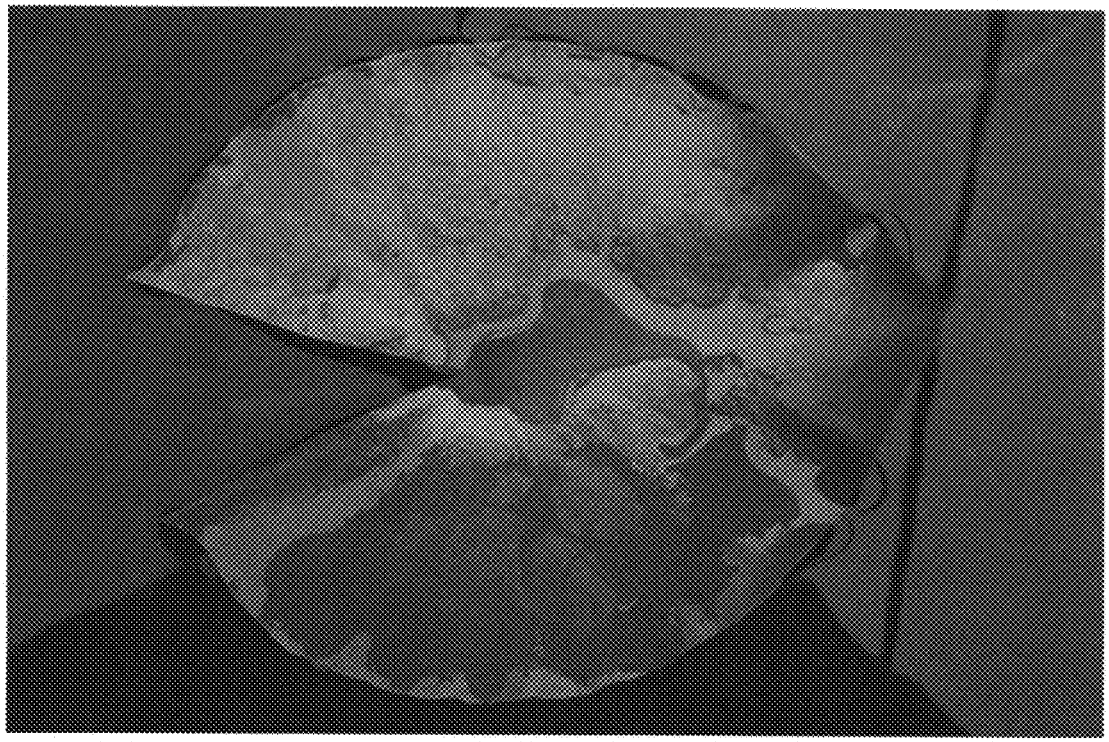
FIG. 4 is a top view of one leaf of a water lily plant of my new variety at the approximate age of one year.
Figure 5:
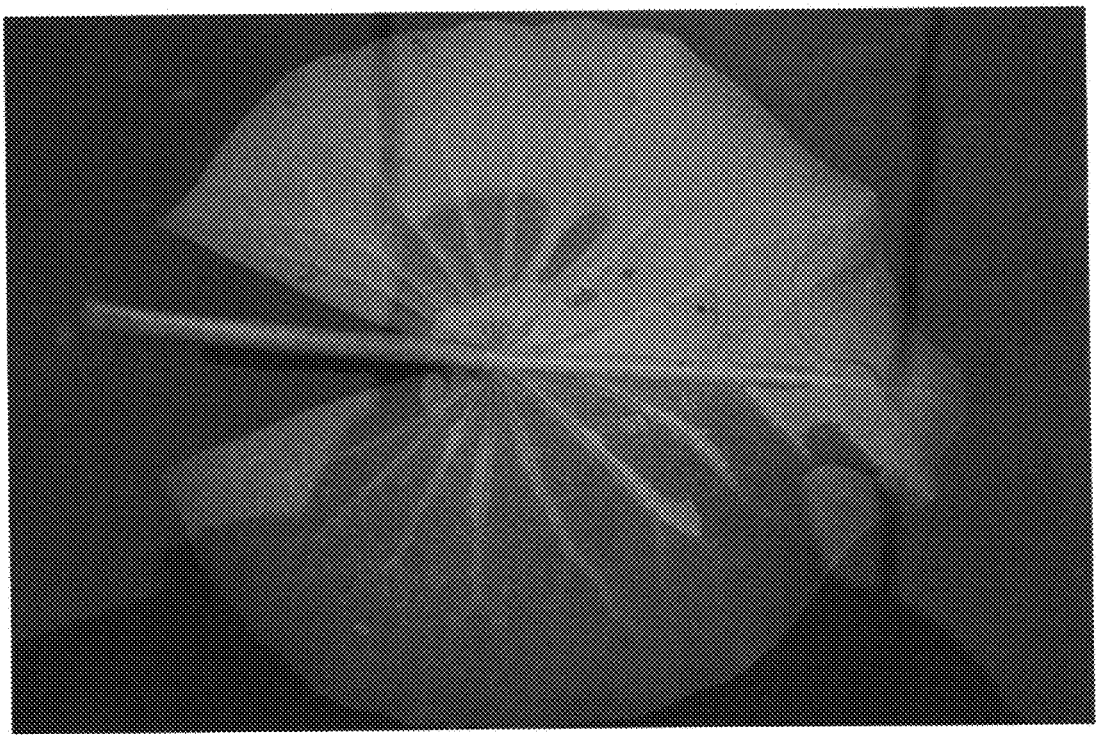
FIG. 5 is a bottom view of one leaf of a water lily plant of my new variety at the approximate age of one year.
Figure 6:
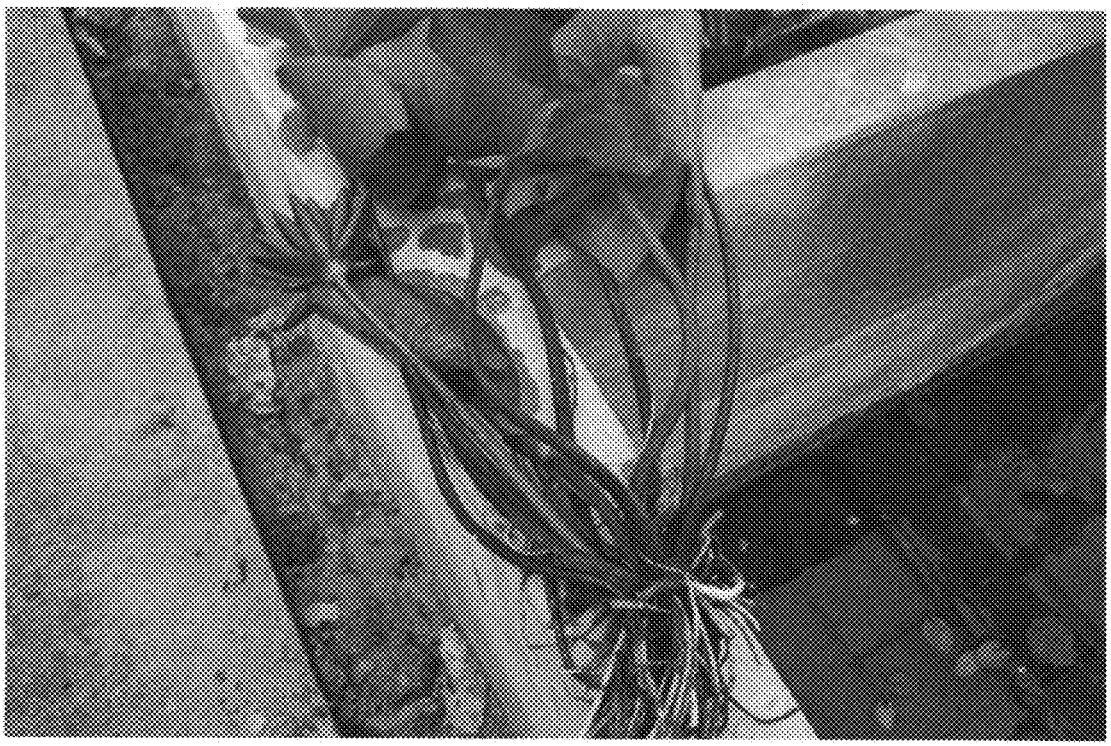
FIG. 6 is a view of a plant of my new variety at the approximate age of one year showing a portion of its rhizome.

The following is a detailed description of the invention based on observations of a water lily plant of my new variety that resulted from asexual propagation by rhizome division in Davie, Fla. Characteristics described below are based on observations of a one-year old plant growing in a dirt bottom concrete tank in Davie, Fla.

PLANT

Origin: From a lily breeding program carried out in Davie, Broward County, Fla.

Parentage:

*Seed parent.*—*Nymphaea* 'Bernice Ikins'.

*Pollen parent.*—*Nymphaea* '109'.

Commercial classification: Ornamental Water Lily Plant.

*Vigor.*—Normal vigor for a *Nymphaea* water lily. A one-year old plant typically covers an overall area of 3-4 feet on the surface of a pond when grown at Davie, Fla.

*Age at maturity.*—One-year.

*Rhizome.*—Grows substantially in horizontal direction, elongating with growth; mature when 1 cm to 3 cm in diameter. New plants grow from mature portions of the rhizome, usually emerging initially as a small cluster of two to 10 stems.

FOLIAGE

*Stem color.*—Green RHS 146 A.

*Plant stems.*—On average, 14 stems per plant. Typical stems are six inches to four feet.

*Leaf stems.*—Flexible.

*Leaf stem diameter.*—7 mm to 12 mm.

*Foliage.*—Typical number of leaves per plant is 8.

*Shape of leaf.*—Overall: Round; Base: Open sinus at base; Apex: round. Shape and depth of any slit: v-shaped, ⅓ the diameter of the leaf. Sinus at base of leaf: Typical 11 cm at base becoming connected at petiole.

*Margins.*—Mostly smooth with slight serrations.

*Leaf arrangement.*—Typically in a circular pattern on the surface of the water. Leaves appear to come alternately off the rhizome.

*Typical leaf size.*—Approximately 20 cm to 26 cm in diameter.

*Venation pattern.*—Not readily evident on the surface of the leaf, but raised in a palmate venation pattern on the underside of the leaf.

*Texture.*—Upper surface: Smooth; Lower surface: Smooth with exposed venation.

*Pubescence on peduncle.*—Pubescent when young; losing substantially all pubescence is associated with maturity of the plant. Color of pubescence: White RHS 156 D.

*Leaf color.*—Upper surface of leaf: Green RHS 137 A. Lower surface of leaf: Olive Green RHS 146 B.

FLOWER

Blooming habit: Blooms continuously throughout the summer months. Up to as many as three flowers open at one time.

Bud:

*Size.*—About 55 mm long and 20 mm in diameter when the petals start to unfurl.

*Form.*—The bud form is long, pointed, ovoid.

*Color.*—When sepals first divide, bud color is Green RHS 83 A; when half open, the upper sides of the petals are Purple RHS 83 A in the center of the flower and Purple RHS 83 A on the edges; and the lower sides of the petals are Purple RHS 83A.

Sepals: Number: 4. Color: Upper (inner) surface: Purple RHS 86 B. Lower (outer) surface: Green RHS 137 A. Length: 55 to 65 mm. Width: 20 mm. Shape: Generally triangular, with a squared base and acute tip. Surface texture: Smooth with slight vertical ribbing. There are-four appendaged sepals.

Receptacle: Color: Yellow RHS 8 A. Shape: circular disc. Size: Average: 1.5 cm diameter, about 15 mm long×15 mm wide. Surface: rough.

Peduncle: Length: Average: 20 cm. Surface: Pubescent. Color: Green RHS 146 B. Strength: Stiff.

Bloom:

*Height.*—Approximately 16 cm from the water surface to the top of the flowers, inclusive of the peduncle.

*Size.*—On average, when fully opened (unfurled), diameter is about 14 to 16 cm.

*Borne.*—One flower per peduncle.

*Flower peduncle.*—Strength: Stiff. Average length depends upon water depth. In 15 cm of water, average length is 30 cm, diameter about 7 to 10 mm. Color of flower peduncle: Green RHS 146 B.

*Number of blooms per peduncle.*—One bloom per stem.

*Form.*—Bloom is a semi-circle with sepals lying flat parallel to the water surface (Bloom is generally round when unfurled, petals on edges). Permanence: Retains its form to the end; outer petal edges curl slightly.

Petals:

*Length.*—Average: 6 cm.

*Width.*—Average: 15 mm.

*Thickness.*—Average: Less than 1 mm.

*Surface texture.*—Upper Surface: Smooth; Lower Surface: Smooth.

*Margin.*—Smooth.

*Apex shape.*—Blunt point.

*Base shape.*—Flat.

*Form.*—Slightly cupped with tips slightly recurved.

*Number.*—Number of petals per flower under normal conditions: 30 to 33.

*Color.*—The upper surfaces of the petals are Purple RHS 86 A in the center of the flower and Purple RHS 86 A on the edges of the flower. The under surfaces of the petals are Purple RHS 86 B. Variegations: None.

*Discoloration.*—No fading over time.

*Fragrance.*—Fragrant with a fruity rose-like character.

Days to bloom: Flowers approximately 30 days after planting in pond under typical natural 25 growing conditions of 20° Celsius night time temperatures.

Reproductive parts:

*Stamens.*—Shape: Lance-like. Number: 55 to 60. Length: 10 to 25 mm.

*Anthers.*—Length: 8 to 15 mm. Color: Purple RHS 79 B. Arrangement: Layered around the circular stigmatic disc.

*Filaments.*—Color: Yellow RHS 15 B. Length: 5 to 10 mm.

*Pollen.*—Color: Yellow RHS 9 A.

*Pistils.*—Number: 1. Color: Yellow RHS 10 A. Length: 10 mm.

*Styles.*—Color: yellow RHS 8 A. Length: 1 t 2 mm.

*Stigmas.*—Color: Yellow — RHS 8 A. Length: 1 mm.

The fruit: Infertile; no fruit.

Cold hardiness: Observed to be cold hardy in the USDA Zone 5b, not yet tested in other hardiness zones.

Pest and disease tolerance: The new cultivar is typical of the genus. No known unusual resistances to pests or diseases.

I claim:

1. A new and distinct variety of water lily plant, substantially as herein shown and described.

* * * * *